United States Patent
Ionkin et al.

(10) Patent No.: US 7,402,345 B2
(45) Date of Patent: Jul. 22, 2008

(54) ELECTROLUMINESCENT IRIDIUM COMPOUNDS WITH FLUORINATED PHENYLPYRIDINE LIGANDS, AND DEVICES MADE WITH SUCH COMPOUNDS

(75) Inventors: Alex Sergey Ionkin, Kennett Square, PA (US); Ying Wang, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 530 days.

(21) Appl. No.: 10/940,876

(22) Filed: Sep. 14, 2004

(65) Prior Publication Data
US 2006/0054861 A1   Mar. 16, 2006

(51) Int. Cl.
*H01L 51/54* (2006.01)
*C09K 11/06* (2006.01)

(52) U.S. Cl. .................... 428/690; 428/917; 313/504; 313/506; 257/40; 257/E51.044; 546/4

(58) Field of Classification Search .............. None
See application file for complete search history.

(56) References Cited

U.S. PATENT DOCUMENTS

| 5,247,190 | A | 9/1993 | Friend et al. |
| 5,408,109 | A | 4/1995 | Heeger et al. |
| 5,552,678 | A | 9/1996 | Tang et al. |
| 2002/0190250 | A1 | 12/2002 | Vladimir et al. |
| 2003/0059646 | A1* | 3/2003 | Kamatani et al. ........... 428/690 |
| 2004/0121184 | A1* | 6/2004 | Thompson et al. .......... 428/690 |

FOREIGN PATENT DOCUMENTS

| EP | 0 443 861 | 8/1991 |
| WO | WO 02/02714 | 1/2002 |
| WO | WO 02/15645 A1 * | 2/2002 |

OTHER PUBLICATIONS

Baldo, et al., "Very high-efficiency green organic light-emitting devices based on electrophosphorescence", Applied Physics Letters, (1999) pp. 4-6, vol. 75, No. 1, New Jersey.

* cited by examiner

*Primary Examiner*—Marie R. Yamnitzky

(57) ABSTRACT

The present invention is generally directed to electroluminescent Ir(III) compounds, the substituted 2-phenylpyridines that are used to make the Ir(III) compounds, and devices that are made with the Ir(III) compounds.

10 Claims, 1 Drawing Sheet

Figure 1 – Schematic of a light-emitting device
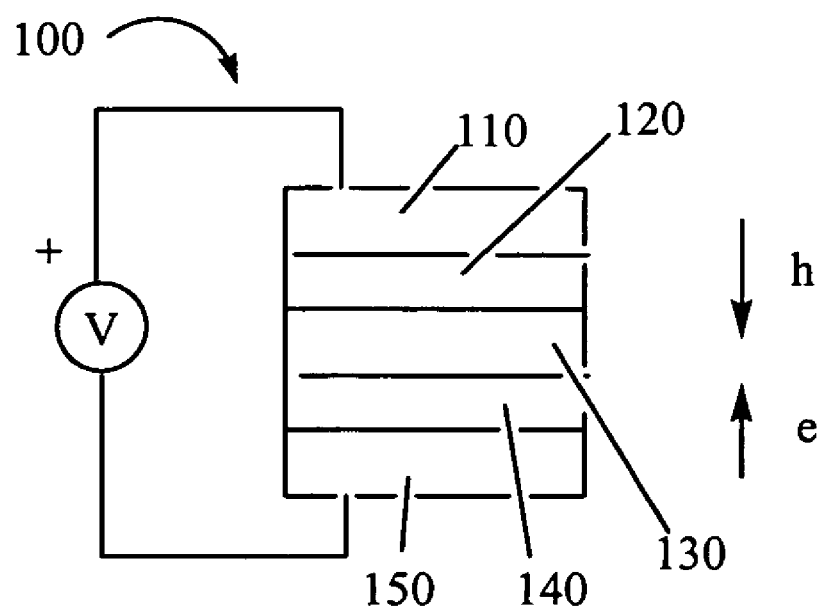

ELECTROLUMINESCENT IRIDIUM COMPOUNDS WITH FLUORINATED PHENYLPYRIDINE LIGANDS, AND DEVICES MADE WITH SUCH COMPOUNDS

BACKGROUND OF THE INVENTION

1. Field of the Invention

This invention relates to electroluminescent complexes of iridium(III) with fluorinated phenylpyridines. It also relates to electronic devices in which the active layer includes an electroluminescent Ir(III) complex.

2. Technical Background

Organic electronic devices that emit light, such as light-emitting diodes that make up displays, are present in many different kinds of electronic equipment. In all such devices, an organic active layer is sandwiched between two electrical contact layers. At least one of the electrical contact layers is light transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Grushin et al., U.S. patent application 2002/0190250, disclose electroluminescent iridium compounds with fluorinated phenylpyridines, and devices made with such compounds.

Burrows and Thompson have reported that fac-tris(2-phenylpyridine) iridium can be used as the active component in organic light-emitting devices. (*Appl. Phys. Lett.* 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-$C'^2$,N]iridium(III). (Polymer Preprints 2000, 41(1), 770.) Electroluminescent iridium complexes having fluorinated phenylpyridine, phenylpyrimidine, or phenylquinoline ligands have been disclosed in published application WO 02/02714.

However, there is a continuing need for electroluminescent compounds.

SUMMARY OF THE INVENTION

The present invention is directed to an iridium compound (generally referred as "Ir(III) compounds") having Formula I:

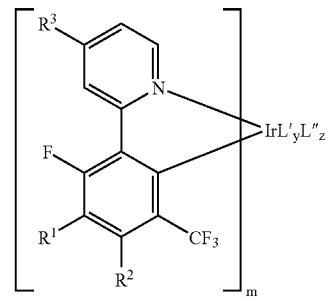

Formula I wherein:

$R^1$=H, F, or $C_nF_{2n+1}$, $R^2$=H, or $C_nF_{2n+1}$ $R^3$=$NO_2$, Me (methyl), or $NR_2$ R=is the same or different at each occurrence and is alkyl, aryl, or adjacent R groups are alkylene or substituted alkylene and can join together to form a 5- or 6-membered ring, L'=a bidentate ligand and is not a phenylpyridine, phenylpyrimidine, or phenylquinoline;

L"=a monodentate ligand, and is not a phenylpyridine, and phenylpyrimidine, or phenylquinoline;

m=1, 2 or 3;

y=0, 1 or 2, z=0, 2 or 4; and n is an integer from 1 through 20, with the proviso that the compound is charge neutral and the iridium is hexacoordinate.

In another embodiment, the present invention is directed to substituted 2-phenylpyridine precursor compounds from which the above Ir(III) compounds are made. The precursor compounds have a Formula II below:

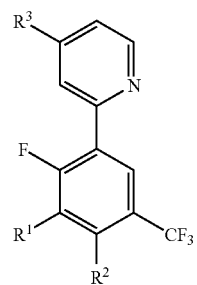

Formula II where $R^1$, $R^2$ and $R^3$ are as defined in Formula I above.

It is understood that there is free rotation about the phenyl-pyridine bond in compounds of Formula II. However, for the discussion herein, the compounds will be described in terms of one orientation.

In another embodiment, the present invention is directed to an organic electronic device having at least one emitting layer comprising the above Ir(III) compound, or combinations of the above Ir(III) compounds.

BRIEF DESCRIPTION OF THE DRAWINGS

FIG. 1 is a schematic diagram of a light-emitting device (LED).

DETAILED DESCRIPTION OF THE INVENTION

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, where "a" and "b" represent different coordinating atoms, having octahedral geometry, in which the three "a" atoms are all adjacent, i.e. at the corners of one face of the octahedron. The term "meridional" is intended to mean one isomer of a complex, $Ma_3b_3$, having octahedral geometry, in which the three "a" atoms occupy three positions such that two are trans to each other. The term "hexacoordinate" is intended to mean that six groups or points of attachment are coordinated to a central metal. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. In the Formulae and Equations, the letters L, R, Y, and Z are used to designate atoms or groups that are defined within. All other letters are used to designate conventional atomic symbols. The term "(H+F)" is intended to mean all combinations of hydrogen and fluorine, including completely hydrogenated, partially fluorinated or perfluorinated substituents.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

One embodiment of the invention comprises compositions of Formula I:

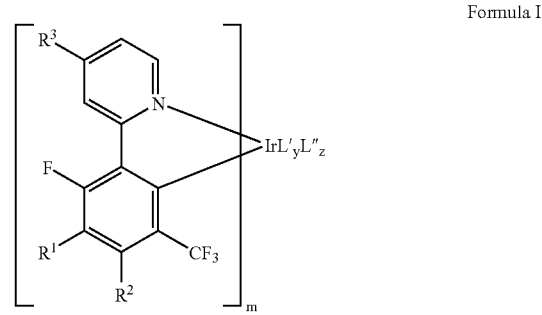

Formula I wherein:
$R^1$=H, F, or $C_nF_{2n+1}$, F
$R^2$=H, or $C_nF_{2n+1}$
$R^3$=$NO_2$, Me (methyl), or $NR_2$
R=is the same or different at each occurrence and is alkyl, aryl, or adjacent R groups are alkylene or substituted alkylene and can join together to form a 5- or 6-membered ring,
L'=a bidentate ligand and is not a phenylpyridine, phenylpyrimidine, or phenylquinoline;
L"=a monodentate ligand, and is not a phenylpyridine, and phenylpyrimidine, or phenylquinoline;
m=1, 2 or 3;
y=0, 1 or 2,
z=0, 2 or 4; and
n is an integer from 1 through 20, with the proviso that the compound is charge neutral and the iridium is hexacoordinate.

In one embodiment, $R^1$ and $R^2$ are H.

In one embodiment of Formula I, L' ligand is a monoanionic bidentate ligand. In general such ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

The β-enolate ligands generally correspond to structures of Formula III

Formula III where $R^5$ is the same or different at each occurrence. The $R^5$ groups can be substituted or unsubstituted alkyl, aryl, alkylaryl or heterocyclic groups. Adjacent $R^5$ and $R^6$ groups can be alkylene or substituted alkylene that are joined to form five- and six-membered rings. In one embodiment, $R^5$ groups are selected from $C_n(H+F)_{2n+1}$, $—C_6H_5$, cyclo-$C_4H_3S$, and cyclo-$C_4H_3O$, where n is an integer from 1 through 20. The $R^6$ group can be H, F, substituted or unsubstituted alkyl, substituted or unsubstituted aryl, alkylaryl, or heterocyclic groups.

Examples of suitable β-enolate ligands include the compounds listed below. The abbreviation for the β-enolate form is given below in brackets.

2,4-pentanedionate [acac]
1,3-diphenyl-1,3-propanedionate [DI]
2,2,6,6-tetramethyl-3,5-heptanedionate [TMH]
4,4,4-trifluoro-1-(2-thienyl)-1,3-butanedionate [TTFA]
7,7-dimethyl-1,1,1,2,2,3,3-heptafluoro-4,6-octanedionate [FOD]
1,1,1,3,5,5,5-heptafluoro-2,4-pentanedionate [F7acac]
1,1,1,5,5,5-hexafluoro-2,4-pentanedionate [F6acac]
1-phenyl-3-methyl-4-i-butyryl-pyrazolinonate [FMBP]

Many β-dicarbonyl parent compounds for the β-enolate ligands are available commercially. The parent compound 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step according to the procedure published in *Izv. AN USSR. Ser. Khim.* 1980, 2827. This compound should be stored and reacted under anhydrous conditions as it is susceptible to hydrolysis.

The hydroxyquinolinate ligands can be substituted with groups such as alkyl or alkoxy groups that may be partially or fully fluorinated. Examples of suitable hydroxyquinolinate ligands include (with abbreviation provided in brackets):

8-hydroxyquinolinate [8hq]
2-methyl-8-hydroxyquinolinate [Me-8hq]
10-hydroxybenzoquinolinate [10-hbq]

Many parent hydroxyquinoline compounds are available commercially.

Phosphino alkoxide ligands generally correspond to structures of Formula IV:

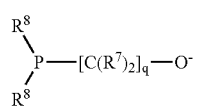

(Formula IV)

where $R^7$ can be the same or different at each occurrence and is selected from H and $C_n(H+F)_{2n+1}$, $R^8$ can be the same or different at each occurrence and is selected from the group of $C_n(H+F)_{2n+1}$, $C_6(H+F)_5$, $C_6H_{5-n}(R^9)_n$, and $(CH_2)_nC(C_n(H+F)_{2n+1})_2OH$;

$R^9=CF_3$, $C_2F_5$, n-$C_3F_7$, i-$C_3F_7$, $C_4F_9$, or $CF_3SO_2$, and q is 2 or 3.

Examples of suitable phosphino alkoxide ligands include (with abbreviation provided in brackets):

3-(diphenylphosphino)-1-oxypropane [dppO]
1,1-bis(trifluoromethyl)-2-(diphenylphosphinoyethoxide [tfmdpeO]

Some of the parent phosphino alkanol compounds are available commercially, or can be prepared using known procedures, such as, for example, the procedure reported for tfmdpeO in *Inorg. Chem.* 1985, v. 24, p. 3680 or in *J. Fluorine Chem.* 2002, 117, 121.

In one embodiment, L' is a ligand coordinated through a carbon atom which is part of an aromatic group. The ligand can have a structure corresponding to Formula V:

 Formula V wherein Ar is an aryl or heteroaryl group, Y is a group having a heteroatom capable of coordinating to Ir, r is 0 or an integer from 1 through 20, p is an integer from 1 through 5, and further wherein one or more of the carbons in $(CH_2)_r$ can be replaced with a heteroatom and one or more of the hydrogens in $(CH_2)_r$ can be replaced with D or F.

In one embodiment, Y is selected from $N(R^{10})_2$, $OR^{10}$, $SR^{10}$, and $P(R^{11})_2$, wherein $R^{10}$ is the same or different at each occurrence and is H, $C_nH_{2n+1}$ or $C_n(H+F)_{2n+1}$ and $R^{11}$ is the same or different at each occurrence and is selected from H, $R^{10}$, Ar and substituted Ar.

In one embodiment, Ar is phenyl, q is 1, Y is $P(Ar)_2$, and p is 1 or 2.

Monodentate ligand L" can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L', such as β-enolates and phosphinoakoxides, can act as monodentate ligands. The monodentate ligand can also be a coordinating anion such as halide, nitrate, sulfate, hexahaloantimonate, and the like. These ligands are generally available commercially.

The monodentate L" ligand can be a non-ionic ligand, such as CO or a monodentate phosphine ligand. The phosphine ligands can a structure corresponding to Formula VI

 Formula VI where Ar' represents an aryl or heteroaryl group. The Ar' group can be unsubstituted or substituted with alkyl, heteroalkyl, aryl, heteroaryl, halide, carboxyl, sulfoxyl, or amino groups. The phosphine ligands are generally available commercially.

In one embodiment of Formula I, the compound is tris-cyclometallated, with m=3 and y=z=0. The compound can be facial, meridional, or a combination of isomers.

In one embodiment of Formula I, m=2. In one embodiment, y=1 and z=0.

In one embodiment of Formula I, m=1. In one embodiment y=1 and z=2. In one embodiment one L" ligand is a hydride and one L' ligand is nonionic. In one embodiment L' is a ligand coordinated through a carbon atom which is part of an aromatic group.

In one embodiment, the complexes having Formula I exhibit blue luminescence. In one embodiment, the complexes have photoluminescent and/or electroluminescent spectra that have a maximum at 500 nm or less. In one embodiment, the maximum is less than 480 nm.

Examples of iridium complexes having Formula I are described in the Examples section, below.

In one embodiment of Formula I, the complex comprises a ligand derived from one or more ligand precursors with the structures shown below:

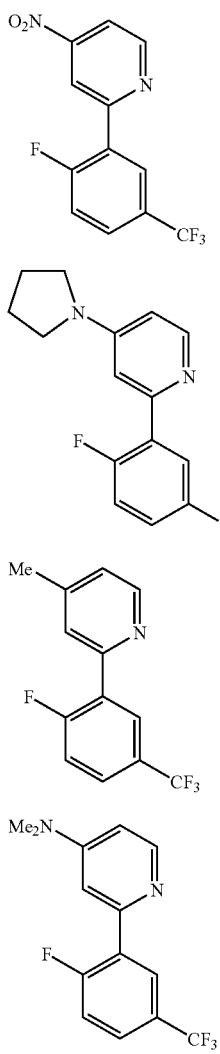

Structure I

Structure II

Structure III

Structure IV

The Ir(III) compounds of this invention are neutral and non-ionic, and can be sublimed intact. Thin films of these materials obtained via vacuum deposition exhibit good to excellent electroluminescent properties. Introduction of fluorine substituents into the ligands on the iridium atom increases both the stability and volatility of the complexes. As a result, vacuum deposition can be carried out at relatively low temperatures and decomposition of the complexes can be avoided. Introduction of fluorine substituents into the ligands can often reduce the non-radiative decay rate and the self-quenching phenomenon in the solid state. These reductions can lead to enhanced luminescence efficiency.

The iridium complexes of the invention are generally prepared from the appropriate substituted 2-phenylpyridine compound. The substituted 2-phenylpyridines, as shown in Formula II above, are prepared, in good to excellent yield, using the Suzuki coupling of the substituted 2-chloropyridine with arylboronic acid as described in O. Lohse, P. Thevenin, E. Waldvogel *Synlett,* 1999, 45-48.

Examples of 2-phenylpyridines include Structures I through IV, shown above.

The 2-phenylpyridines thus prepared are used for the synthesis of the cyclometalated iridium complexes. A convenient one-step method has been developed employing commercially available iridium trichloride hydrate and silver trifluoroacetate. The reactions are generally carried out with an excess of 2-phenylpyridine, without a solvent, in the presence of 3 equivalents of $AgOCOCF_3$. This reaction is illustrated in Equation (1)

Eq. 1

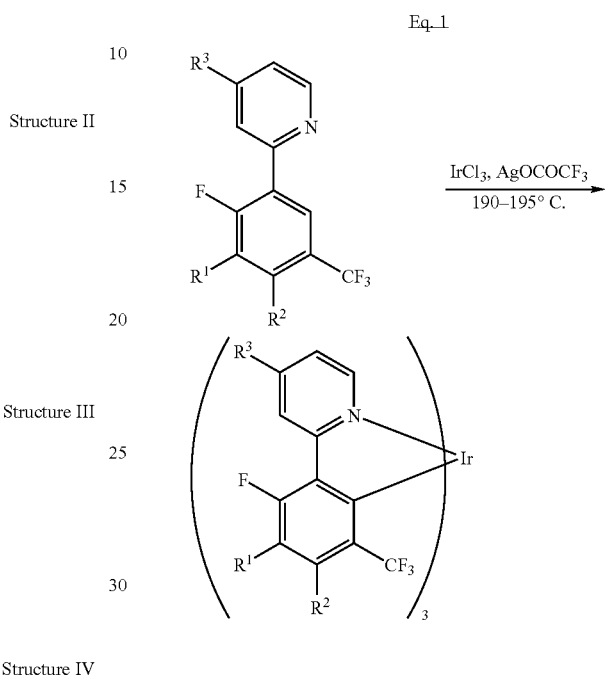

below:

Tris-cyclometalated iridium complexes having Formula I where m=3, can be isolated, purified, and fully characterized by elemental analysis, $^1H$ and $^{19}F$ NMR spectral data, and, for compounds, single crystal X-ray diffraction. In some cases, mixtures of isomers are obtained. Often the mixture can be used without isolating the individual isomers.

Bis-cyclometalated iridium complexes having Formula I where m=2, can, in some cases, be isolated from the reaction mixture using the same synthetic procedures as used for preparing the tris-cyclometalated complexes above. The complexes can also be prepared by first preparing an intermediate iridium dimer

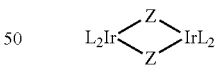

where L is the same or different and is a phenylpyridine ligand, and Z is Cl or $OR^{12}$, where $R^{12}$ is H, $CH_3$, or $C_2H_5$. The iridium dimers can generally be prepared by first reacting iridium trichloride hydrate with the 2-phenylpyridine and optionally adding $NaOR^{12}$. Reaction of the dimer with L' and/or L" gives the compound of Formula I of this invention.

In an improved process for preparing bis-cyclometalated iridium complexes, the chloro-bridged iridium dimer is prepared by reacting iridium (III) chloride trihydrate with the appropriate ligand precursor in trimethylphosphate.

Mono-cyclometalated iridium complexes of the invention can, in some cases, be isolated from reaction mixtures formed by the above-described processes. Such mono-cyclometalated species can be favored by use of phosphine-containing ligands such as that shown in Formula VI and by using a stoichiometric excess of such ligands (>2 equivalents per Ir). These materials can be isolated from the reaction mixture by standard techniques, such as chromatography on silica with methylene chloride eluent.

Electronic Device

The present invention also relates to an electronic device comprising at least one photoactive layer positioned between two electrical contact layers, wherein the at least one layer of the device includes the iridium complex of the invention. Devices frequently have additional hole transport and electron transport layers. A typical structure is shown in FIG. 1. The device 100 has an anode layer 110 and a cathode layer 150. Adjacent to the anode is a layer 120 comprising hole transport material. Adjacent to the cathode is a layer 140 comprising an electron transport material. Between the hole transport layer and the electron transport layer is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The iridium compounds of the invention are particularly useful as the photoactive material in layer 130, or as electron transport material in layer 140. Preferably the iridium complexes of the invention are used as the light-emitting material in diodes. It has been found that in these applications, the fluorinated compounds of the invention do not need to be in a solid matrix diluent in order to be effective. A layer that is greater than 20% by weight iridium compound, based on the total weight of the layer, up to 100% iridium compound, can be used as the emitting layer. This is in contrast to the non-fluorinated iridium compound, tris(2-phenylpyridine) iridium (III), which was found to achieve maximum efficiency when present in an amount of only 6-8% by weight in the emitting layer. This dilution was necessary to reduce the self-quenching effect. Additional materials can be present in the emitting layer with the iridium compound. For example, a fluorescent dye may be present to alter the color of emission. A diluent may also be added and such diluent may be a charge transport material or an inert matrix. A diluent may comprise polymeric materials, small molecule or mixtures thereof. A diluent may act as a processing aid, may improve the physical or electrical properties of films containing the iridium compound, may decrease self-quenching in the iridium compounds described herein, and/or may decrease the aggregation of the iridium compounds described herein. Non-limiting examples of suitable polymeric materials include poly(N-vinyl carbazole) and polysilane. Non-limiting examples of suitable small molecules includes 4,4'-N,N'-dicarbazole biphenyl or tertiary aromatic amines. When a diluent is used, the iridium compound is generally present in a small amount. In one embodiment, the iridium compound is less than 20% by weight, based on the total weight of the layer. In one embodiment, the iridium compound is less than 10% by weight, based on the total weight of the layer.

In some cases the iridium complexes may be present in more than one isomeric form, or mixtures of different complexes may be present. It will be understood that in the above discussion of OLEDs, the term "the iridium compound" is intended to encompass mixtures of compounds and/or isomers.

To achieve a high efficiency LED, the HOMO (highest occupied molecular orbital) of the hole transport material should align with the work function of the anode, the LUMO (lowest un-occupied molecular orbital) of the electron transport material should align with the work function of the cathode. Chemical compatibility and sublimation temp of the materials are also important considerations in selecting the electron and hole transport materials.

The other layers in the OLED can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1-18 (CRC Handbook of Chemistry and Physics, 81$^{st}$ Edition, 2000). The anode 110 may also comprise an organic material such as polyaniline as described in "Flexible light-emitting diodes made from soluble conducting polymer," *Nature* vol. 357, pp 477-479 (11 Jun. 1992). At least one of the anode and cathode should be at least partially transparent to allow the generated light to be observed.

Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate.

Examples of electron transport materials for layer 140 include metal chelated oxinoid compounds, such as tris(8-hydroxyquinolato)aluminum ($Alq_3$); phenanthroline-based compounds, such as 2,9-dimethyl4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole transport layer 120, 50-1000 Å, preferably 200-800 Å; light-emitting layer 130, 10-1000 Å, preferably 100-800 Å; electron transport layer 140, 50-1000 Å, preferably 200-800 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the iridium compounds of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The iridium complexes of the invention often are phosphorescent and photoluminescent and may be useful in applications other than OLEDs. For example, organometallic complexes of iridium have been used as oxygen sensitive indicators, as phosphorescent indicators in bioassays, and as catalysts. The bis cyclometalated complexes can be used to sythesize tris cyclometalated complexes where the third ligand is the same or different.

EXAMPLES

The following examples illustrate certain features and advantages of the present invention. They are intended to be illustrative of the invention, but not limiting. All percentages are by weight, unless otherwise indicated.

Tris(dibenzylideneacetone) dipalladium was purchased from Alfa-Aesar (Ward Hill, Mass.). 2-Chloro-4-nitropyridine was purchased from Lancaster Synthesis Company (Windham, N.H.). 2,2-Bis-trifluoromethyl-oxirane is available from E.I. duPont de Nemours and Co. (Wilmington, Del.).

Di-tert-butyl-trimethylsilylmethyl-phosphane ($^tBu_2P$—$CH_2$—$SiMe_3$) was prepared as follows: 50.00 g (0.277 mol) of di-t-butylchlorophosphine, 304 ml of 1.0 M pentane solution of (trimethylsilylmethyl)lithium and 150 ml of THF) were refluxed under argon for 3 days. The reaction mixture was allowed to cool to RT and an aqueous solution of ammonium chloride was added slowly. The organic phase was separated, and dried with magnesium sulfate. After removal of the solvent, the product was purified by distillation under vacuum and used in the examples below.

MPMP was prepared in a manner similar to that for bis(4-diethylamino-2-methylphenyl)phenylmethane, as described in U.S. Pat. No. 4,053,311 (Example 1), except that p-tolualdehyde was substituted for benzaldehyde.

All other reagents were purchased and used as received from Sigma-Aldrich Co. (Milwaukee, Wis.), unless otherwise indicated.

Example 1

Synthesis of 2-(2-Fluoro-5-trifluoromethyl-phenyl)-4-methyl-pyridine

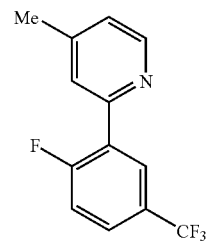

10.0 g (0.0481 mol) of 2-fluoro-5-(trifluoromethyl)phenylboronic acid, 5.52 g (0.0433 mol) of 2-chloro-4-methyl-pyridine, 1.10 g (0.0012 mol) of tris(dibenzylideneacetone) dipalladium (0), 0.67 g (0.00289 mol) of di-tert-butyl-trimethylsilylmethyl-phosphane, 8.0 g (0.0527 mol) of cesium fluoride and 100 ml of dioxane were stirred at room temperature for 24 hours. The resultant mixture was poured into 200 ml of water and extracted twice with 200 ml of methylene chloride. The organic phase was dried on magnesium sulfate overnight and filtered. The solvent was removed on a rotovapor and the residue was purified by chromatography on silica gel with petroleum ether/ethyl ether (10/0.5) as eluent. Yield of 2-(2-fluoro-5-trifluoromethyl-phenyl)-4-methyl-pyridine: 4.70 g (42.57%) as a colorless liquid. ¹H NMR (CD₂Cl₂) 2.30 (s, 3H, Me), 6.90-8.50 (m, 6H, arom-H). ¹⁹F NMR (CD₂Cl₂) −63.75 (s, 3F, CF3), −112.44 (s, 1F, F-arom). LC/MS calculated for C₁₃H₉F₄N 255.07; found 255.07.

Example 2 a. Di-μ-chlorotetrakis[3-fluoro-6-trifluoromethyl-2-(4-methyl-2-pyridinyl-κN)phenyl-κC]-di-iridium

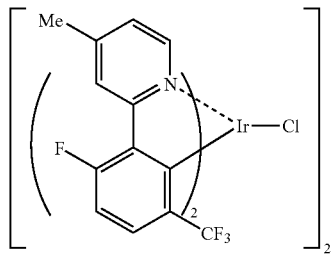

4.7 g (0.0184 mol) of 2-(2-fluoro-5-trifluoromethyl-phenyl)-4-methyl-pyridine, 2.92 g (0.00828 mol) of iridium (III) chloride trihydrate, and 30 ml of trimethylphosphate were stirred at 90° C. for 6 hours under the flow of nitrogen. The precipitate was filtered and dried under 1.0 mm vacuum. The yield of the dimer was 6.45 g (95.27%). The crude above chlorodimer was used "as it is" in the next steps. The yield of the dimer was 6.45 g (95.27%) as yellow powder.

b. Bis[3-fluoro-6-trifluoromethyl-2-(4-methyl-2-pyridinyl-κN)phenylκC](2,2,6,6-tetramethyl-3,5-heptanedionato-κO,κO')-iridium

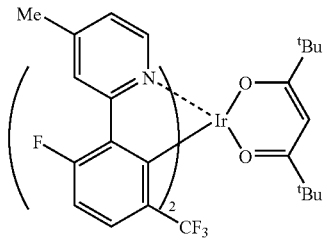

2.5 g (0.00170 mol) of di-μ-chlorotetrakis[3-fluoro-6-trifluoromethyl-2-(4-methyl-2-pyridinyl-κN)phenyl-κC]di-iridium, 1.25 g (0.00678) of 2,2,6,6-tetramethyl-heptane-3,5-dione, 1.77 g of 55-60% solution of tetrabutylammonium hydroxide in water and 30 ml of THF were refluxed for 2 hours under argon atmosphere. The reaction mixture was poured into 200 ml of water and extracted twice with 200 ml of diethyl ether. The extracts were dried over magnesium sulfate overnight. The solvent was removed on a rotavapor and the residue was purified by chromatography on silica gel with using petroleum ether/ethyl ether (10/0.5) as eluent. Yield of bis[3-fluoro-6-trifluoromethyl-2-(4-methyl-2-pyridinyl-κN)phenyl-κC](2,2,6,6-tetramethyl-3,5-heptanedionato-κO,κO')-iridium: 2.41 g (80.31%) as a yellow solid with m.p. 351.47° C. ¹H NMR (CD₂Cl₂) 0.60 (s, 18H t-Bu), 2.25 (s, 3H, Me), 6.40-8.10 (m, 10H, arom-H). ¹⁹F NMR (CD₂Cl₂) −58.68 (s, 6F, CF3), −111.76 (s, 2F, F-arom). Anal. Found: C, 50.28; H, 3.99; F, 17.20. The structure was confirmed by X-ray analysis.

Example 3

Bis[3-fluoro-6-trifluoromethyl-2-(4-methyl-2-pyridinyl-κN)phenyl-κC]([3-(phenyl((3,3,3-trifluoro-2-hydroxy-2-trifluoromethyl)phosphino)-1,1,1-trifluoro-2-(trifluoromethyl)-2-propanolato-κO,κP])-iridium a. 1,1,1,3,3,3-Hexafluoro-2-{[phenyl-(3,3,3-trifluoro-2-hydroxy-2-trifluoromethyl-propyl)-phosphanyl]-methyl}-propan-2-ol Phenylphosphane (10.0 g, 0.0908 mol) and 2,2-bis-trifluoromethyl-oxirane (35.98 g, 0.20 mol) were stirred at room temperature for 3 months under nitrogen. The resulted viscous liquid was recrystalized from pentane at −35° C. The yield of 1,1,1,3,3,3-hexafluoro-2-{[phenyl-(3,3,3-trifluoro-2-hydroxy-2-trifluoromethyl-propyl)-phosphanyl]-methyl}-propan-2-ol was 27.14 g (63.55%) as a colorless solid with no m.p. below 200° C. ¹H NMR (CD2Cl2) 3.10 (m, 4H CH2), 6.40-7.50 (m, 10H, arom-H). ¹⁹F NMR (CD2Cl2) −58.68 (m, 12F, CF3). ³¹P NMR (CD2Cl2) −41.31. Anal. Found: C, 35.83; H, 2.49. The structure was confirmed by X-ray analysis.

b. Bis[3-fluoro-6-trifluoromethyl-2-(4-methyl-2-pyridinyl-κN)phenyl-κC]([3-(phenyl((3,3,3-trifluoro-2-hydroxy-2-trifluoromethyl)phosphino)-1,1,1-trifluoro-2-(trifluoromethyl)-2-propanolato-κO, κP])-iridium

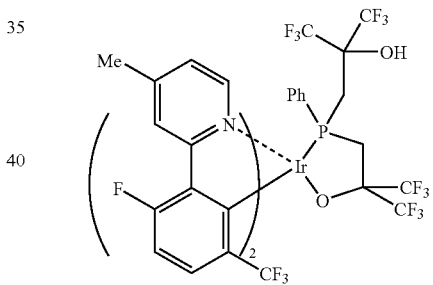

2.0 g (0.00136 mol) of di-μ-chlorotetrakis[3-fluoro-6-trifluoromethyl-2-(4-methyl-2-pyridinyl-κN)phenyl-κC]di-iridium, 3.19 g (0.00678) of 1,1,1,3,3,3-hexafluoro-2-{[phenyl-(3,3,3-trifluoro-2-hydroxy-2-trifluoromethyl-propyl)-phosphanyl]-methyl}-propan-2-ol, 1.41 g of 55-60% solution of tetrabutylammonium hydroxide in water and 30 ml of THF were refluxed for 2 hours under argon atmosphere. The reaction mixture was poured in 200 ml of water and extracted twice with 200 ml of diethyl ether. The extracts were dried over magnesium sulfate overnight. The solvent was removed on a rotavapor and the residue was purified by chromatography on silica gel with petroleum ether/ethyl ether (10/0.5) as eluent. Yield of bis[3-fluoro-6-trifluoromethyl-2-(4-methyl-2-pyridinyl-κN)phenyl-κC]([3-(phenyl((3,3,3-trifluoro-2-hydroxy-2-trifluoromethyl)phosphino)-1,1,1-trifluoro-2-(trifluoromethyl)-2-propanolato-κO,κP])-iridium: 2.03 g (68.35%) as a yellow solid with m.p. 312.27° C. ¹H NMR (DMSO-D6) 1.04 (s, 1H, CH2-CF3), 1.45-1.88 (br, 1H, CH2-CF3), 2.67 (s, 3H, Me), 2.80 (b, 2H, CH2-CF3) 6.60-9.01 (m, 15H, arom-H). ³¹P NMR (DMSO-D6) 5.79. Anal. Found: C, 37.37; H, 1.94; F, 34.77.

Example 4

2-(2-Fluoro-5-trifluoromethyl-phenyl)-4-nitro-pyridine

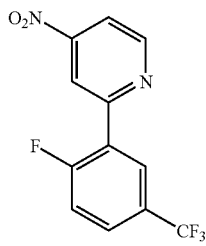

10.0 g (0.0481 mol) of 2-fluoro-5-(trifluoromethyl)phenylboronic acid, 6.86 g (0.0433 mol) of 2-chloro-4-nitropyridine, 1.10 g (0.0012 mol) of tris(dibenzylideneacetone) dipalladium (0), 0.67 g (0.00289 mol) of di-tert-butyl-trimethylsilylmethyl-phosphane, 15.67 g (0.0481 mol) of cesium carbonate and 100 ml of dioxane were stirred at room temperature for 24 hours. The resultant mixture was poured into 200 ml of water and extracted twice with 200 ml of methylene chloride. The organic phase was dried over magnesium sulfate overnight and filtered. The solvent was removed on a rotovapor and the residue was purified by chromatography on silica gel with petroleum ether/ethyl ether (10/0.5) as eluent. Yield of 2-(2-fluoro-5-trifluoromethyl-phenyl)-4-nitro-pyridine: 3.58 g (28.92%) as a white solid with m.p. 58.11° C. $^1$H NMR (CD$_2$Cl$_2$) 7.10-8.90 (m, 6H, arom-H). $^{19}$F NMR (CD$_2$Cl$_2$) −62.98 (s, 3F, CF3), −111.85 (s,1F, F-arom). LC/MS calculated for C$_{12}$H$_6$F$_4$N$_2$O$_2$ 286.04; found 286.04.

Example 5 a. Di-μ-chlorotetrakis[3-fluoro-6-trifluoromethyl-2-(4-nitro-2-pyridinyl-κN)phenyl-κC]di-iridium

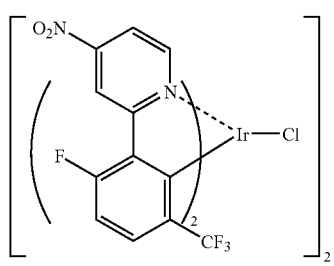

3.58 g (0.0125 mol) of 2-(2-fluoro-5-trifluoromethyl-phenyl)-4-nitro-pyridine, 1.98 g (0.00562 mol) of iridium (III) chloride trihydrate, and 20 ml of trimethylphosphate were stirred at 90° C. for 6 hours under the flow of nitrogen. The precipitate was filtered and dried under 1.0 mm vacuum. The yield of the dimer was 4.90 g (95.27%). The crude above chlorodimer was used "as it is" in the next steps. The yield of the dimer was 4.90 g (98.20%) as red powder.

b. Bis[3-fluoro-6-trifluoromethyl-2-(4-nitro-2-pyridinyl-κN)phenyl-κC]([3-(di-pheny/phosphino)-1,1,1-trifluoro-2-(trifluoromethyl)-2-propanolato-κO, -κP])-iridium

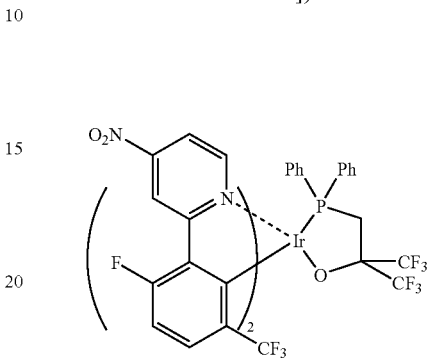

4.8 g (0.003 mol) of di-μ-chlorotetrakis[3-fluoro-6-trifluoromethyl-2-(4-nitro-2-pyridinyl-κN)phenyl-κC]di-iridium, and 0.00962 mol of lithium 2-[(diphenylphosphanyl)-methyl]-1,1,1,3,3,3-hexafluoro-propan-2-olate in 40 ml of THF were stirred at room temperature for 24 hours. The reaction mixture was purified by chromatography on silica gel with petroleum ether/ethyl acetate (10/0.5) as eluent. Yield of bis[3-fluoro-6-trifluoromethyl-2-(4-nitro-2-pyridinyl-κN)phenyl-κC]([3-(di-phenylphosphino)-1,1,1-trifluoro-2-(trifluoromethyl )-2-propanolato-κO,-κP])-iridium: 2.25 g (33.19%) as red solid with m.p. 318.09° C. $^1$H NMR (CD$_2$Cl$_2$) 2.80-3.15 (m, 2H, CH2-CF3), 6.55-9.05 (m, 20H, arom-H). $^{19}$F NMR (CD$_2$Cl$_2$) −56.99 (s, 3F, CF3), −58.37 (s, 3F, CF3), −74.01 (s, 3F, CF3), −79.81 (s, 3F, CF3), −108.86 (s,1F, F-arom), −109.27 (s,1F, F-arom). $^{31}$P NMR (CD$_2$Cl$_2$) 13.74. Anal. Found: C, 42.63; H, 1.91; N, 5.03; P, 2.98. The structure was confirmed by X-ray analysis.

Example 6

Bis[3-fluoro-6-trifluoromethyl-2-(4-pyrrolidin-1-yl-2-pyridinyl-κN)phenyl-κC]([3-(di-phenylphosphino)-1,1,1-trifluoro-2-(trifluoromethyl)-2-propanolato-κO, -κP])-iridium a. Lithium 2-[(diphenylphosphanyl)-methyl]-1,1,1,3,3,3-hexafluoro-propan-2-olate Lithium diphenylphosphide (2.20 g, 0.0115 mol) was dissolved in 20 ml of THF and cooled to −35° C. 2,2-Bis-trifluoromethyl-oxirane (2.06 g, 0.0114 mol) was added at the same temperature in one portion. After 1 hour the reaction mixture contained only one chemical shift in the $^{31}$P-NMR spectrum at −27.17 ppm, which is consistent with the structure. The solution was used "as it is" in the next step.

b. Bis[3-fluoro-6-trifluoromethyl-2-(4-pyrrolidin-1-yl-2-pyridinyl-κN)phenyl-κC]([3-(di-phenylphosphino)-1,1,1-trifluoro-2-(trifluoromethyl)-2-propanolato-κO, -κP])-iridium

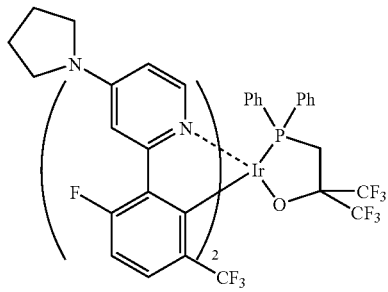

1.0 g (0.00089 mol) of bis[3-fluoro-6-trifluoromethyl-2-(4-nitro-2-pyridinyl-κN)phenyl-κC]([3-(di-phenylphosphino)-1,1,1-trifluoro-2-(trifluoromethyl)-2-propanolato-κO, -κP])-iridium and 30 ml of pyrrolidine were refluxed 1 hour under nitrogen. The solvent was removed in 1 mm vacuum. The reaction mixture was purified by chromatography on silica gel using petroleum ether/ethyl acetate (10/1) as eluent. Yield of bis[3-fluoro-6-trifluoromethyl-2-(3-pyrrolidin-1-yl-2-pyridinyl-κN)phenyl-κC]([3-(di-phenylphosphino)-1,1,1-trifluoro-2-(trifluoromethyl)-2-propanolato-κO, -κP])-iridium: 0.67 g (64.26%) as a yellow solid with m.p. 305.68° C. $^1$H NMR (CD$_2$Cl$_2$) 2.08 (s, 4H, pyrrol), 2.80-3.15 (m, 2H, CH2-CF3), 3.30 (s, 4H, pyrrol), 6.60-8.45 (m, 20H, arom-H). $^{19}$F NMR (CD$_2$Cl$_2$) -56.54 (s, 3F, CF3), -58.00 (s, 3F, CF3), -73.44 (s, 3F, CF3), -78.90 (s, 3F, CF3), -111.73 (s, 1F, F-arom), -113.14 (s, 1F, F-arom). $^{31}$P NMR (CD$_2$Cl$_2$) 10.92. Anal. Found: C, 49.27; H, 3.34; N, 4.81; P, 2.85. The structure was confirmed by X-ray analysis.

Example 7

Bis[3-fluoro-6-trifluoromethyl-2-(4-dimethylamino-2-pyridinyl-κN)phenyl-κC]([3-(di-phenylphosphino)-1,1,1-trifluoro-2-(trifluoromethyl)-2-propanolato-κO, -κP])-iridium and

[3-fluoro-6-trifluoromethyl-2-(4-dimethylamino-2-pyridinyl-κN)phenyl-κC], [3-fluoro-6-trifluoromethyl-2-(4-nitro-2-pyridinyl-κN)phenyl-κC]([3-(di-phenylphosphino)-1,1,1-trifluoro-2-(trifluoromethyl)-2-propanolato-κO, -κP])-iridium

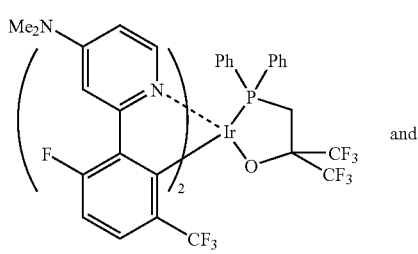

and

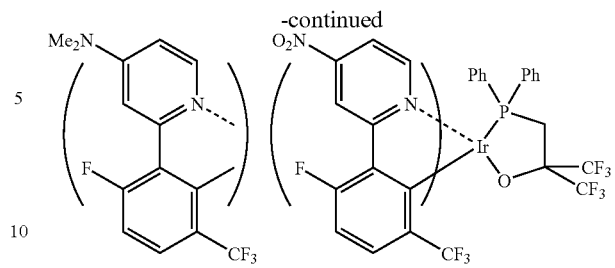

1.0 g (0.00089 mol) of bis[3-fluoro-6-trifluoromethyl-2-(4-nitro-2-pyridinyl-κN)phenyl-κC]([3-(di-phenylphosphino)-1,1,1-trifluoro-2-(trifluoromethyl)-2-propanolato-κO, -κP])-iridium, and 50 ml of 1 M solution of dimethylamine in THF were refluxed for 48 hours under nitrogen. The solvent was removed in 1 mm vacuum and the reaction mixture was purified by chromatography on silica gel with petroleum ether/ethyl acetate (10/1) as eluent. The first compound to eluate from the chromatographic column was of bis[3-fluoro-6-trifluoromethyl-2-(4-dimethylamino-2-pyridinyl-κN)phenyl-κC]([3-(di-phenylphosphino)-1,1,1-trifluoro-2-(trifluoromethyl)-2-propanolato-κO, -κP])-iridium. Yield of bis[3-fluoro-6-trifluoromethyl-2-(4-dimethylamino-2-pyridinyl-κN)phenyl-κC]([3-(di-phenylphosphino)-1,1,1-trifluoro-2-(trifluoromethyl)-2-propanolato-κO, -κP])-iridium: 0.24 g (23.45%) as red solid with m.p. 317.27° C. $^1$H NMR (CD$_2$Cl$_2$) 2.80-2.90 (m, 1H, CH2-CF3), 2.95 (s, 6H, Me2N), 3.10 (s, 6H, Me2N), 3.15-3.25 (m, 1H, CH2-CF3), 6.40-8.20 (m, 20H, arom-H). $^{19}$F NMR (CD$_2$Cl$_2$) -56.63 (s, 3F, CF3), -58.12 (s, 3F, CF3), -73.55 (s, 3F, CF3), -78.96 (s, 3F, CF3), -111.90 (s,1F, F-arom), -113.23 (s, 1F, F-arom).). $^{31}$P NMR (CD$_2$Cl$_2$) 10.77. Anal. Found: C, 47.11; H, 3.08; N, 5.17 P, 2.81. The structure was confirmed by X-ray analysis.

The second compound to eluate from the chromatographic column was iridium, [3-fluoro-6-trifluromethyl-2-(4-dimethylamino-2-pyridinyl-κN)phenyl-κC], [3-fluoro-6-trifluoromethyl-2-(4-nitro-2-pyridinyl-κN)phenyl-κC]([3-(di-phenylphosphino)-1,1,1-trifluoro-2-(trifluoromethyl)-2-propanolato-κO, -κP])—. Yield of [3-fluoro-6-trifluromethyl-2-(4-dimethylamino-2-pyridinyl-κN)phenyl-κC], [3-fluoro-6-trifluoromethyl-2-(4-nitro-2-pyridinyl-κN) phenyl-κC]([3-(di-phenylphosphino)-1,1,1-trifluoro-2-(trifluoromethyl)-2-propanolato-κO, -κP])-iridium was 0.42 g (42.17%) as yellow solid with m.p. 312.56° C. $^1$H NMR (CD$_2$Cl$_2$) 2.90-3.00 (m, 1H, CH2-CF3), 3.15 (s, 6H, Me2N), 3.20-3.30 (m, 1H, CH2-CF3), 6.40-8.20 (m, 20H, arom-H). $^{19}$F NMR (CD$_2$Cl$_2$) -56.64 (s, 3F, CF3), -58.44 (s, 3F, CF3), -73.49 (s, 3F, CF3), -79.31 (s, 3F, CF3), -111.07 (s, 1F, F-arom), -111.11 (s, 1F, F-arom).). $^{31}$P NMR (CD$_2$Cl$_2$) 12.92. Anal. Found: C, 44.90; H, 2.59 N, 5.11; P, 2.93. The structure was confirmed by X-ray analysis.

Example 8

OLED devices were fabricated by the thermal evaporation technique. The base vacuum for all of the thin film deposition was in the range of 10$^{-6}$ torr. The deposition chamber was capable of depositing eight different films without the need to break up the vacuum.

Patterned indium tin oxide (ITO) coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to $10^{-6}$ torr. The substrate was then further cleaned using an oxygen plasma for about 5 minutes. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

The OLED samples were characterized by measuring their (1) current-voltage (I-V) curves, (2) electroluminescence radiance versus voltage, and (3) electroluminescence spectra versus voltage. The I-V curves were measured with a Keithley Source-Measurement Unit Model 237. The electroluminescence radiance (in the unit of $cd/m^2$) vs. voltage was measured with a Minolta LS-110 luminescence meter, while the voltage was scanned using the Keithley SMU. The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table I summarizes device configuration and efficiency of OLED devices fabricated using materials disclosed in the present invention. MPMP is the hole transport material, DPA is the electron transport material, and AIQ is the electron injection material. Their molecular structures are shown in the following:

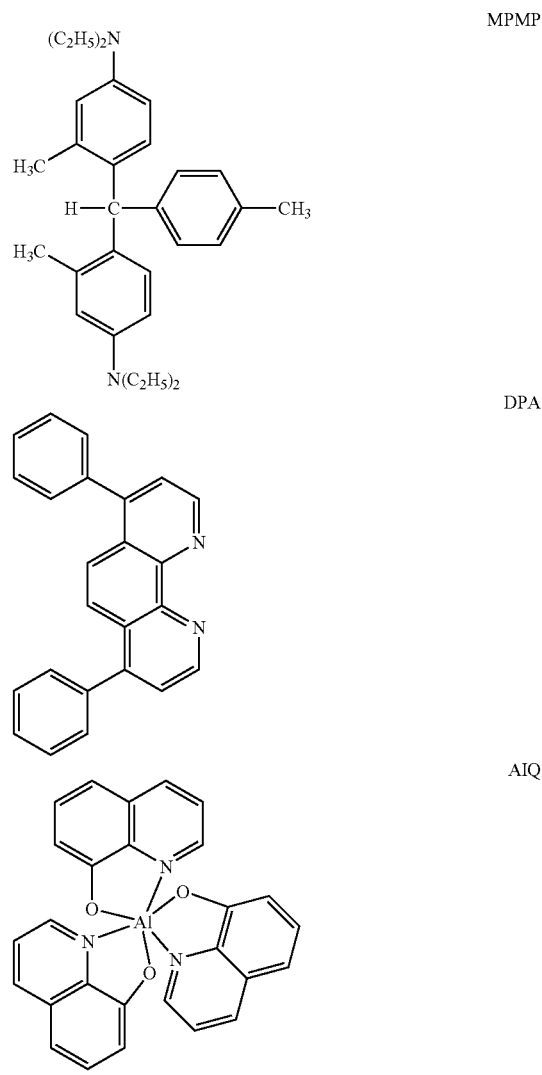

TABLE I

Device configurations and efficiency of OLED devices

| Emitter | Device configuration | Efficiency cd/A | Radiance cd/m2 | Peak wavelength nm | Color coordinates |
|---|---|---|---|---|---|
| Emitter 1 | MPMP(302 Å)/Emitter 1(402 Å)/DPA(103 Å)/ AlQ(302 Å)/LiF(10 Å)/ Al(505 Å); | 1 at 14 V | 70 at 20 V | 465 | (0.243, 0.403) |

TABLE I-continued

Device configurations and efficiency of OLED devices

| Emitter | Device configuration | Efficiency cd/A | Radiance cd/m2 | Peak wavelength nm | Color coordinates |
|---|---|---|---|---|---|
| Emitter 2 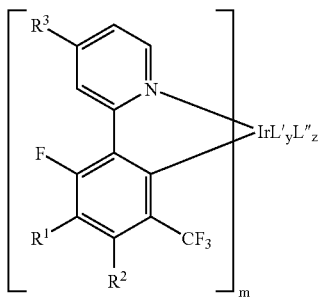 | MPMP(303 Å)/Emitter 2(402 Å)/DPA(105 Å)/ AlQ(301 Å)/LiF(10 Å)/ Al(504 Å); | 10 at 13 V | 6500 at 19 V | 470 | (0.217, 0.494) |

What is claimed is:

1. An organic electronic device comprising at least one layer comprising a composition of Formula I

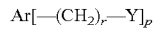

Formula I

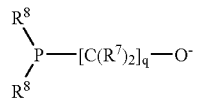

wherein:
R$^1$=H, F, or C$_n$F$_{2n+1}$;
R$^2$=H, or C$_n$F$_{2n+1}$;
R$^3$=NO$_2$, Me (methyl) or NR$_2$;
R=is the same or different at each occurrence and is alkyl, aryl, or adjacent R groups are alkylene or substituted alkylene and can join together to form a 5- or 6-membered ring;
L'=a bidentate ligand and is not a phenylpyridine, phenylpyrimidine, or phenylquinoline;
L''=a monodentate ligand, and is not a phenylpyridine, phenylpyrimidine, or phenylquinoline;
m=1 or 2;
y=1 or 2;
z=0 or 2; and
n is an integer from 1 through 20,
with the proviso that the composition is charge neutral and the iridium is hexacoordinate;
and wherein at least one L' is a phosphino alkoxide ligand of Formula IV:

$$R^8\text{-P-}[C(R^7)_2]_q\text{-O}^-$$ (Formula IV)
with R$^8$ on P where
R$^7$ can be the same or different at each occurrence and is selected from H and C$_n$(H+F)$_{2n+1}$;
R$^8$ can be the same or different at each occurrence and is selected from the group of C$_n$(H+F)$_{2n+1}$, C$_6$(H+F)$_5$, C$_6$H$_{5-n}$(R$^9$)$_n$, and (CH$_2$)$_n$C(C$_n$(H+F)$_{2n+1}$)$_2$OH;
R$^9$=CF$_3$, C$_2$F$_5$, n-C$_3$F$_7$, i-C$_3$F$_7$, C$_4$F$_9$, or CF$_3$SO$_2$; and
q is 2 or 3
or
L' is selected from the group of ligands having structure according to Formula V:

$$\text{Ar}[-(CH_2)_r-Y]_p$$ Formula V wherein
Ar is phenyl;
Y is P(Ar)$_2$;
r is 0 or an integer from 1 through 20;
p is 1 or 2, wherein the carbon in one or more of the (CH$_2$) can be replaced with a heteroatom and one or more of the hydrogens in one or more of the (CH$_2$) can be replaced with D or F
and wherein if m=2, then each occurrence of

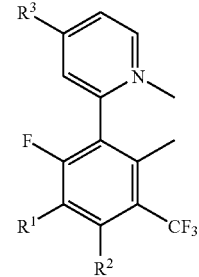

can be the same or different.

2. The device of claim 1, wherein R$^1$ and R$^2$=H.

3. The device of claim 1, wherein the phosphino alkoxide ligand is

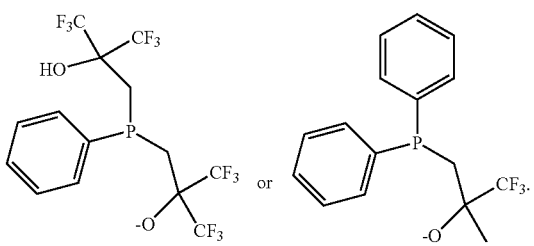

4. The device of claim 1, wherein z=2 and at least one of L" is a non-ionic ligand.

5. The device of claim 1, wherein z=2 and at least one of L" is an anionic ligand.

6. The device of claim 1, wherein the composition is selected from the group of compounds with structures V, VIII and IX:

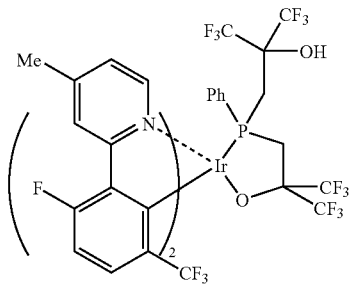

Structure V

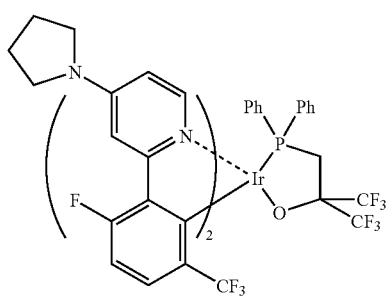

Structure VIII

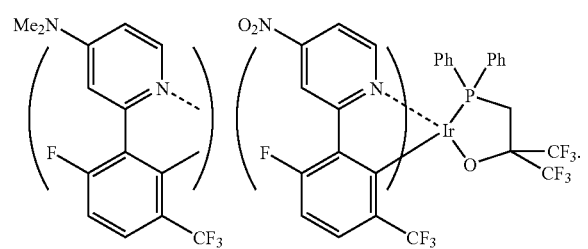

Structure IX

7. The device of claim 1, further comprising a diluent selected from the group consisting of poly(n-vinyl carbazole), polysilane, 4,4'-N,N'-dicarbazole biphenyl, and tertiary amines.

8. The device of claim 1, further comprising a hole transport layer comprising a compound selected from the group consisting of: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), porphyrinic compounds, and combinations thereof.

9. The device of claim 1, further comprising an electron transport layer comprising a compound selected from the group consisting of tris(8-hydroxyquinolato)aluminum (Alq$_3$); 2,9-dimethyl-4,7-diphenyl-1,10-phenanthroline (DDPA); 4,7-diphenyl-1,10-phenanthroline (DPA); 2-(4-biphenylyl)-5-(4-t-butylphenyl)-1,3,4-oxadiazole (PBD); 3-(4-biphenylyl)-4-phenyl-5-(4-t-butylphenyl)-1,2,4-triazole (TAZ) and combinations thereof.

10. A composition having a structure selected from Structures V, VIII and IX:

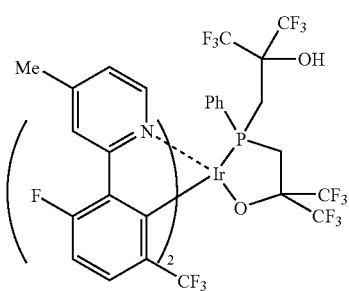

Structure V

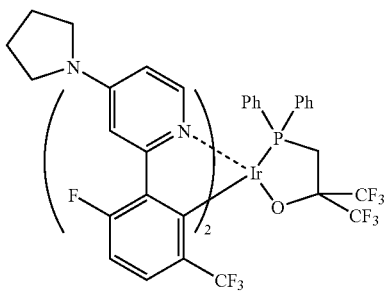

Structure VIII

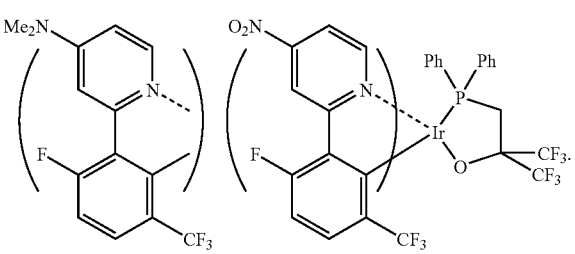

Structure IX

* * * * *